United States Patent [19]

Clark

[11] 4,124,905
[45] Nov. 14, 1978

[54] ARTIFICIAL INTRAOCULAR LENS SYSTEM
[75] Inventor: James A. Clark, Mendon, N.Y.
[73] Assignee: Bausch & Lomb Incorporated, Rochester, N.Y.
[21] Appl. No.: 736,908
[22] Filed: Oct. 29, 1976
[51] Int. Cl.$^2$ .......................... A61F 1/16; A61F 1/24
[52] U.S. Cl. ..................................... 3/13; 128/303 R
[58] Field of Search .......................................... 3/13, 1

[56] References Cited
U.S. PATENT DOCUMENTS

3,906,551  9/1975  Otter ............................................ 3/13
3,991,426  11/1976 Flom et al. .................................. 3/13
3,994,027  11/1976 Jensen et al. ............................... 3/13

Primary Examiner—Ronald L. Frinks
Attorney, Agent, or Firm—Robert S. Beiser; Frank C. Parker

[57] ABSTRACT

An artificial intraocular lens system is provided with posterior and anterior tabs adapted to receive and hold a pin substantially perpendicularly therebetween. Said lens system allows for the insertion and affixing of the lens in the eye without the use of sutures and without requiring incisions in the iris to be made by the surgeon. Also disclosed is a tool for insertion of a lens system into the eye.

27 Claims, 21 Drawing Figures

ARTIFICIAL INTRAOCULAR LENS SYSTEM

BACKGROUND OF THE INVENTION

1. Field of the Invention

This invention relates to artificial intraocular lens systems employed in ophthalmology for the correction of aphakia; and more particularly this invention relates to the lens support system for positioning and affixing the lens in the eye after a natural lens extraction. The invention further relates to a mechanical tool employed in inserting the lens system into the eye.

2. Description of the Prior Art

Presently, there are three distinct methods employed in the art of correcting aphakia resulting from a cataract extraction. In accordance with one practice, the aphakic patient is fitted with a powerful spectacle lens, which lens provides the correction required to restore useful vision to the aphakic eye. The ophthalmic lenses designed to correct an aphakic condition are highly undesirable because they are extremely thick, heavy, and tend to distort the wearer's appearance. The patient suffers from cosmetic discomfort, restricted peripheral vision, distortion of peripheral images, poor binocular vision, scotoma, and reduced ability to clearly focus.

According to the second practice, the patient is fitted with a contact lens. The contact lens overcomes many of the disadvantages associated with spectacles. However, because cataracts are usually a problem associated with the elderly who have lost much of their dexterity, such contact lenses are not desirable.

The third practice developed in the late 1940's when Harold Ridly inserted the first artificial intraocular lens into a human eye. Believing that the artificial lens belongs "where nature intended the crystalline to be", he inserted the artificial lens in the posterior chamber of the eye. The posterior chamber is that area between the iris and the vitreous humor where the natural lens is located i.e., rearwardly the iris.

In the early 1950's, and as a result of medical complications which often occurred after a postpupillary insertion, lenses were developed for insertion in the anterior chamber of the eye. The anterior chamber being that area normally occupied by aqueous humor and being between the iris and the cornea i.e., forwardly of the iris.

Throughout the evolution of the art of correcting aphakia, the shape of the artificial intraocular lens has remained substantially unchanged. The art has primarily concentrated on developing and improving ways for affixing the lens within the interior of the eye. To date, there have developed several methods of lens fixation such as posterior chamber fixation, anterior chamber fixation, iris fixation, iridocapsular fixation, and capsular fixation. Typical fixation means are disclosed in U.S. Pat. Nos. 3,922,728 of Krasnov, 3,913,148 of Potthast, 3,906,551 of Otter, 3,866,249 of Flom, 3,711,870 of Deitrick, and 3,673,616 of Fedorov, et al.

Typically, the artificial intraocular lenses of the prior art are biconvex, planoconvex or concavoconvex in shape and have a power in the range of about +8 to +25 diopters as measured in the aqueous. As compared with the natural lens of the human eye, the artificial lenses are relatively heavy.

Artificial lenses of the prior art have a number of disadvantages. The typical iris clip lens rely on the constrictor muscles of the iris as the positioning means. The iris is therefore maintained in the state of tension, is prevented from assuming a normal shape and the clips obstruct full and normal constriction. Often the operating physician sutures the iris to clips or holes drilled into the lens so as to secure and properly position the lens. The suture materials normally employed are known to disintegrate and dissolve over a period of time. As the suture material disappears positive fixation of the lens can be lost. In place of sutures some lenses require flexible wires which are caused to penetrate through the iris and engage a loop or other engaging means. The surgical steps are difficult especially for a relatively inexperienced physician; and the positioning and placement of these flexible wires require that the physician make an incision in the iris.

SUMMARY OF THE INVENTION

In accordance with the present invention there is provided an artificial intraocular lens system which is extremely simple to implant. The implantation does not require either suturing of the lens to the iris or incisions of the iris. The lens system upon implantation is positively fixed to the iris. The lens does not interfere with the normal constriction or the dilation of the iris. There are no small diameter metal wires which will place a strain upon the iris. The density of the lens can be made to approach the density of the liquid in which the lens is surrounded after implantation thereby reducing harmful affects associated with the movement of the lens due to inertial effects.

The lens system of this invention comprises an optical zone and means for supporting the lens in the eye. The lens may be supported in the anterior chamber, posterior chamber or iris plane of the eye. The improvement of this lens over the prior art comprises at least one pair of anterior and posterior tabs which extend from the periphery or circumferential edge of the optical zone. The tabs are oppositely disposed and spaced apart a distance sufficient to receive a portion of the iris therebetween without substantially interfering with the constriction and dilation of the iris. The anterior tab includes an opening adapted to receive and allow the passage of a pin therethrough. The anterior tab and the posterior tab cooperate to hold the pin substantially perpendicular therebetween whereby the pin having penetrated through the iris obtains a lens positively fixed in the eye.

Preferably one end of the pin is anchored into the lens so that during the surgical implantation, the pin cannot be lost. The support system further includes additional anterior and posterior haptics such as haptic rims, loops, rods and/or tabs as supporting means for the lens.

The invention further includes a medical tool or device for insertion of the lens into the eye. The tool comprises generally first, second and third relatively movable members. The first and second members are adapted to grip the anterior tab portion of the lens system. The third member is adapted to engage a pivotable pin provided on said lens system to move said pin relative to said tab.

Further features of the invention will become apparent from the following description read with reference to diagrammatic drawings wherein like numbers refer to like parts.

DRAWINGS

FIG. 12 is a section view illustrating still another aspect of the pin of this invention;

DESCRIPTION OF THE PREFERRED EMBODIMENTS

Figure 1:
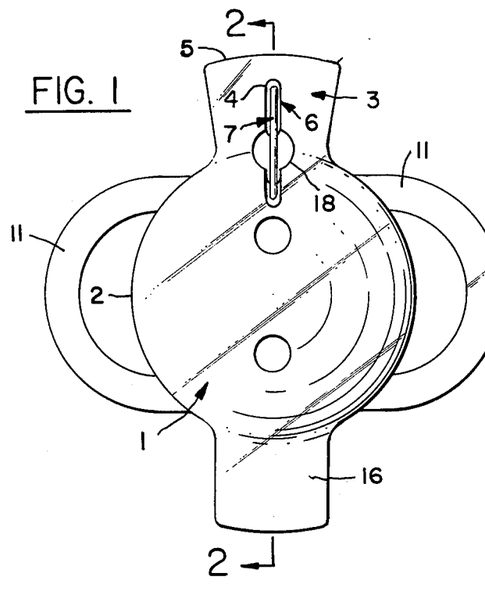
FIG. 1 is a plan view of a lens system according to the present invention.
Figure 2:
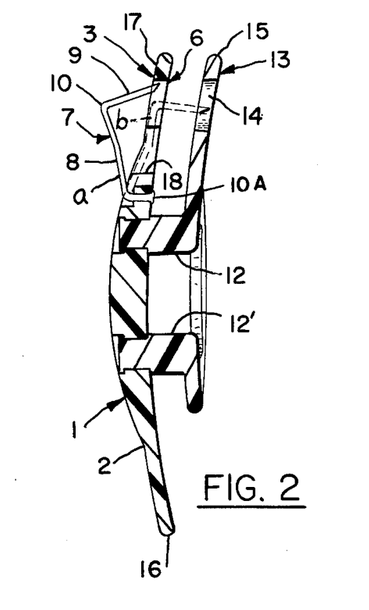
FIG. 2 is a section view taken along the line 2—2 of FIG. 1.

Referring to the drawings, FIGS. 1 and 2 there is illustrated an intraocular lens system according to this invention. As shown, the system comprises an optical zone 1. Extending from a portion of the circumferential edge 2 of the optical zone 1 is anterior tab 3 provided with elongated hole 4 positioned inwardly from tab edge 5, a groove 6 is provided so as to run longitudinally of tab 3 and extends from slightly inwardly the optical zone 1 to hole 4. The groove can be cut completely through the tab so as to provide an elongated hole or it can be formed by carving out a portion of the tab material. Hereinafter the structure 6 shall be referred to as a groove but should be understood to include a hole. Embedded into and pivotably secured into the anterior side of the lens system and slightly inwardly the circumferential edge of optical zone 1 is pin 7 having generally straight portion 8, hook portion 9, bight portion 10 and end 10A. In one embodiment end 10A is ball shaped and is anchored in a socket shaped depression in edge 2, thereby providing a ball and socket joint. Posteriorly, the optical zone is loop 11 having extensions 12 and 12' securely embedded in optical zone 1. Loop 11 is provided with an extension forming a posterior tab 13 provided with hole or groove 14 inwardly from posterior tab edge 15. Anterior tab 3 and posterior tab 13 are oppositely disposed and spaced apart a distance sufficient to receive a portion of the iris of the eye therebetween without interfering with the dilation and constriction of said iris. Extending in generally the opposite direction from tab 3 is tab 16 thereby providing additional supportive means of the lens system on the eye. Loop extensions 12 and 12' are embedded at a sufficient distance from optical zone circumferential edge 2 such that the iris can dilate and constrict without interference.

In accordance with this invention pivotable should be understood to include bendable. The pin is constructed of a malleable material. Pin 7 should be of a sufficient length such that upon bending the pin inwardly, hook portion 9 passes through hole 4 and is received by hole 14 the tabs 3 and 13 cooperating to hold hook portion 9 substantially perpendicular therebetween. Furthermore, in the preferred embodiment groove 6 receives straight pin portion 8 such that the straight pin portion is substantially flush with or slightly lower than the anterior surface 17 of tab 3.

In operation, upon partially opening the cornea and removal of the natural lens, the lens system is placed in the eye with pin 7 in an open position. Loop 11 and posterior tab 13 is positioned posteriorly the iris and tab 3 anteriorly the iris.

Figure 7:
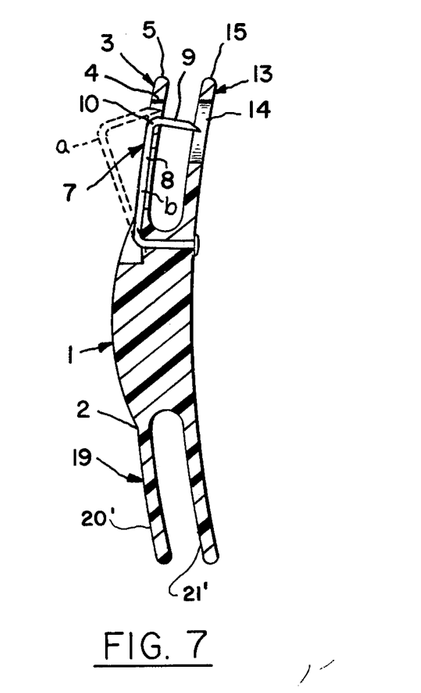
FIG. 7 is a section view taken along the line 7—7 of FIG. 6.
Figure 15:
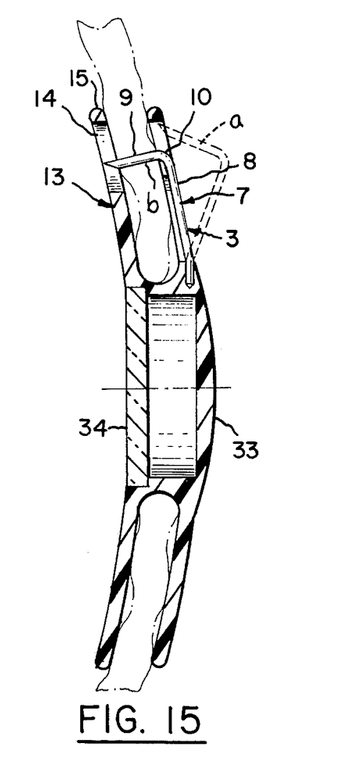
FIG. 15 is a section view taken along lines 15—15 of FIG. 14 and showing the iris positioned within the lens.

Upon properly positioning the lens in the eye, pin 7 is bent inwardly to position b. In the process pin portion 9 punctures through the iris (not shown) and thereby positive affixes the lens system into the eye without the need of sutures and without the need of the operating physician manually cutting incisions into the iris. To facilitate the puncturing of the iris the pin can be chiseled or pointed at its free end as illustrated in FIGS. 2, 7 and 15. As discussed further on a tool facilitating insertion of the lens system is described.

In an especially preferred embodiment of the invention the anterior surface 17 of tab 3 is provided with a depression 18 in the form of a slot or hole (hereinafter referred to as slot) located inwardly from hole 4 and forwardly from the place of securing the pin to the lens. As understood hereinafter, the slot can be carved from a portion of the tab material or it can be formed by cutting through the tab to form a hole. In the event it is necessary to remove the lens system from the eye, hole or slot 18 facilitates such removal for one simply places a surgical instrument into the slot and raises the pin into open position a. In order to facilitate such an operation, slot 18 should desirably extend slightly transverse and perpendicular to groove 6.

Figure 3:
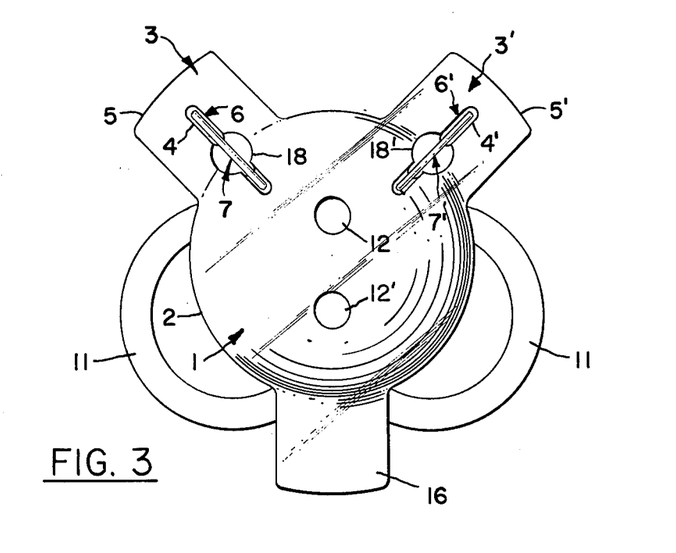
FIG. 3 is a plan view of another embodiment according to the invention.

The lens system of FIG. 3 illustrates a slightly different arrangement in order to obtain positive fixation of the lens system in the eye. The lens system of FIG. 3 is provided with a pair of anterior tabs 3 and 3' extending from a portion of the circumferential edge 2 to optical zone 1. The tabs illustrated herein are shown slightly offset from each other, however, they may be simply arranged to extend parallel to each other. Oppositely disposed from anterior tabs 3 and 3' and spaced apart therefrom are posterior tabs 13 and 13', (not shown), extending from loop 11. The lens further includes pins 7 and 7' arranged to pass through hole 4 and 4' so as to be received in posterior tabs (not illustrated). The lens system further should preferably contain groove 6 and 6' and slot 18 and 18'.

Figure 4:
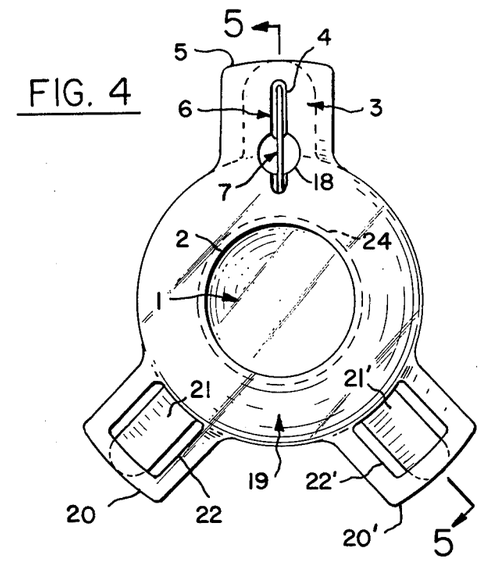
FIG. 4 is a plan view of a lightweight intraocular lens according to this invention.
Figure 5:
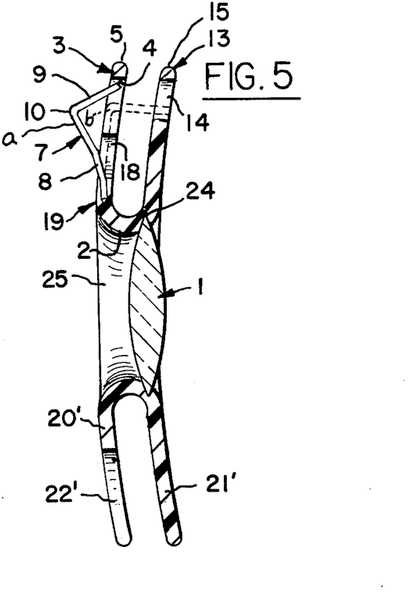
FIG. 5 is a section view taken along the line 5—5 of FIG. 4.

FIGS. 4 and 5 illustrate another arrangement of the lens system in accordance with this invention. In accordance with this embodiment, the lens system is substantially reduced in weight. As illustrated, optical zone 1 is provided to be embedded in annular haptic rim 19 which is U shaped in cross-section so as to receive a portion of the iris thereabout. Haptic rim 19 is further provided with extensions in the form of anterior tab 3, posterior tab 13 and anterior tabs 20 and 20' and posterior tabs 21 and 21'. Tabs 20 and 21' are oppositely disposed and spaced apart from tabs 21 and 21' so as to receive a portion of the iris therein whereby constriction and dilation of the iris is not substantially obstructed or interferred with by these haptic support means. As described above posterior tab 13 is oppositely disposed and spaced apart from tab 3 and provided with hole 14 for receiving the free end of hook portion 9 of pin 7. Pin 7 is preferably secured and embedded in haptic rim 19 at a point slightly outwardly from the inner portion of said rim.

In order to reduce the weight of the lens system, tabs 20 and 20' are provided with holes 22 and 22' of substantial size.

Posteriorly within the inner portion of haptic rim, there is provided groove 24. By slightly bending the rim, lens optical zone 1 in the shape of a convex lens is inserted into the groove 24 and locked in place upon snapping haptic rim back into normal position. As illustrated in FIGS. 4 and 5, the U shaped annular haptic rim is in the form of a collar button having a hollow 25 in its center thereby providing a hole for the passage of light.

Upon inserting the lens illustrated in FIGS. 4 and 5 into the eye, optical zone 1 would be situated in the posterior chamber of the eye. By placing groove 24 essentially within the apex of the U shaped rim the lens system can be arranged such that upon insertion optical zone 1 would be situated substantially within the iris plane of the eye.

Figure 6:
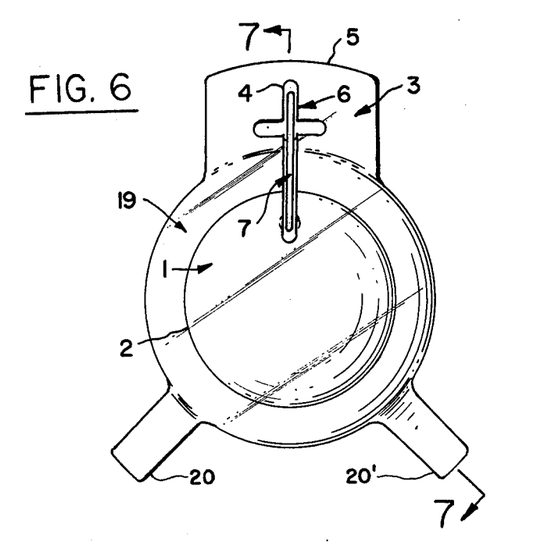
FIG. 6 is a plan view of another embodiment of this invention.

FIGS. 6 and 7 illustrate another lens system configuration. The circumferential edge 2 of optical zone 1 has extending therefrom an annular haptic rim 19 of U-shaped cross-section. Anterior tab 3 and posterior tab 13 extend from a portion of the haptic rim and are provided with holes 4 and 14 to receive and hold perpendicularly therebetween hook portion 9 of pin 7. The secured end of pin 7 is embedded in the optical zone slightly inwardly from the circumferential edge of said optical zone. Additional supportive means are provided by anterior tabs 20 and 20' and posterior tabs 21 and 21', (not shown). However, these tabs may be substituted with loops, rods, or other well-known means for support of intraocular lenses.

The slot means 18 is shown here as a groove or hole crossing groove 9 transverse as compared with the round shaped depression described in the previous figures.

Figure 8:
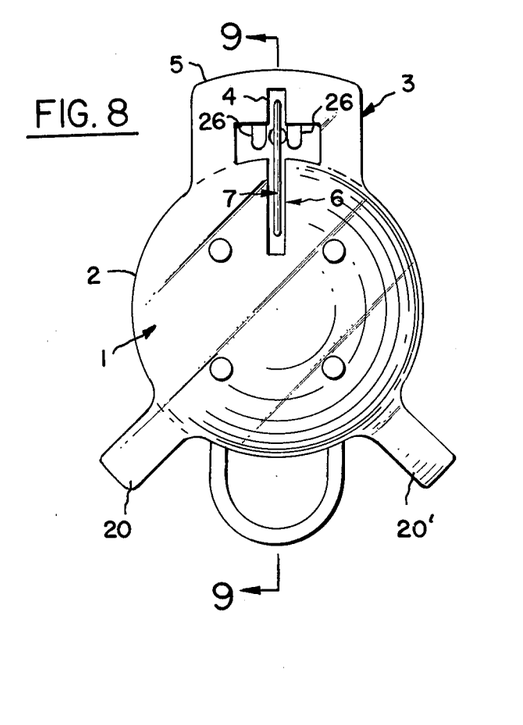
FIG. 8 is a plan view of another intraocular lens of this invention.
Figure 9:
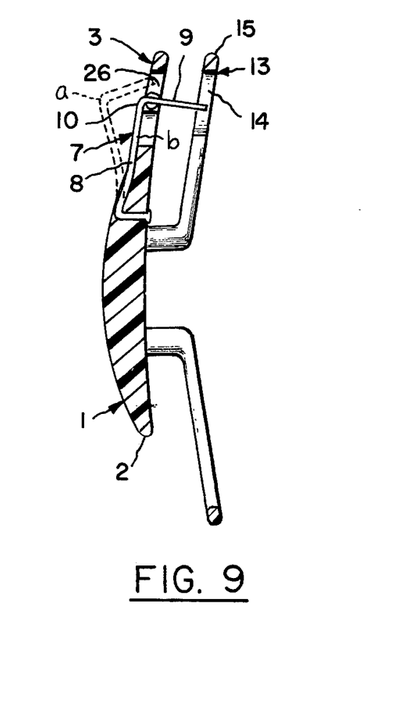
FIG. 9 is a section view taken along the line 9—9 of FIG. 8.

FIGS. 8 and 9 illustrate still another lens system combination comprising posterior tab 13 and anterior tab 3 for receiving a pin 7 perpendicularly therebetween. As illustrated, Anterior tab 3 includes locking means 26 so as to hold the pin securely upon the pin being inwardly pushed into position b.

Figure 10:
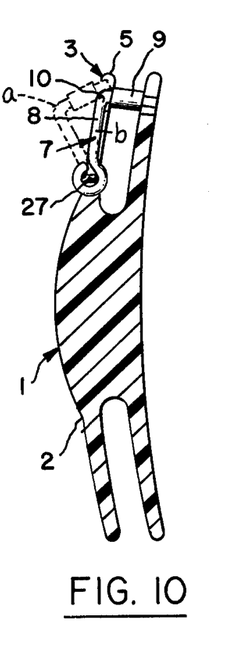
FIG. 10 is a section view showing another aspect of the pin of this invention.

FIGS. 10, 11, 12 and 13 illustrate additional means of securing pin 7 perpendicularly between the anterior and posterior tabs. In FIG. 10 there is illustrated a pin which is pivotally secured to a hinge pin 27 embedded in the haptic rim portion of the anterior tab 3. The hooked portion is further provided with shoulders which prevent forward or backward movement of said pin upon said pin being inwardly pivoted to a position b.

Figure 11:
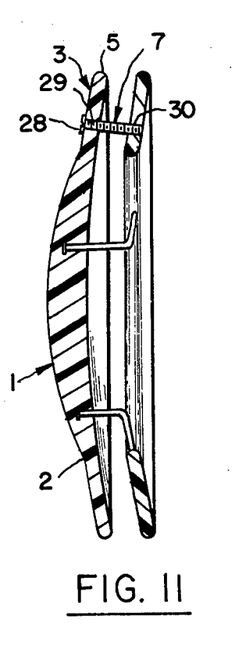
FIG. 11 is a section view illustrating yet another aspect of the pin of this invention.

FIG. 11 illustrates a threaded pin 28 which is received by threaded holes 29 and 30 of anterior and posterior tabs 3 and 13. In operation the lens comprising optical zone 1 and haptic rims, rods and/or loops would be positioned in the eye and thereafter the operating physician would merely screw threaded pin 28 into threaded holes 29 and 30 thereby penetrating the iris located in the posterior and anterior haptic parts so as to positively fix the lens in the eye.

FIG. 12 illustrates another form of pin and locking means. The straight pin 7 is passed through holes 4 and 14 and positioned as in c. The portion of the pin extending outwardly beyond the anterior tab 3 is then bent down and secured into the groove 31 which is cut into anterior tab 3.

Figure 13:
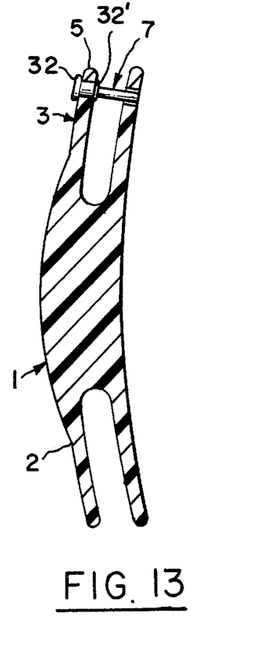
FIG. 13 is a section view illustrating another aspect of the pin of this invention.

FIG. 13 illustrates another form of pin 7 wherein the pin is provided with detents 32 and 32' thereby preventing removal of the pin which is secured and positively affixed through the iris.

Figure 14:
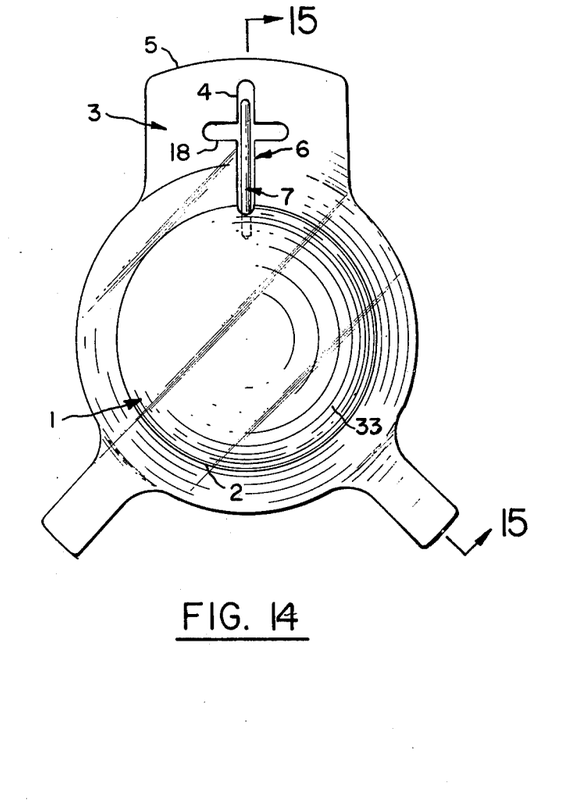
FIG. 14 is a plan view of yet another embodiment of this invention.

In another embodiment of the invention there is provided an intraocular lens which is essentially weightless relative to the median in which the lens is surrounded. In FIGS. 14 and 15, there is illustrated an intraocular lens system comprising an annular haptic rim of U-shaped cross-section further including tab extensions 3 and 13 including holes 4 and 14 and pivotable pin 7 having straight portion 8 and hook portion 9 connected by bight portion 10, groove 6 and slot 18 for facilitating easy removal of the pin should such a need arise. The optical zone 1 is contained within the annular haptic rim including a high plus lens 33 and spaced apart therefrom a plano lens 34. The space therebetween being airtight. The absence of material between the plano and plus lens further reduces the weight of this lens system. In addition to the space between the plano and plus lens one may further reduce the weight of this lens system by cutting holes in various portions of the haptic rim and other supporting means.

Figure 16:
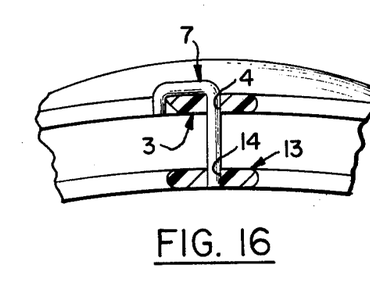
FIG. 16 is a section view showing another aspect of the pin of this invention.
Figure 17:
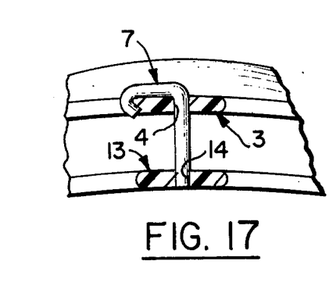
FIG. 17 shows pin of FIG. 16 in fixed position.

FIGS. 16 and 17 illustrate another modification of maintaining the pin in position. In accordance with this embodiment the pin is inserted through holes 4; and 14 and the pin extension is bent over the edge of anterior tab 3 which is provided with a shoulder for receiving said bent portion of the pin.

The materials of which the intraocular lens system of this invention can be formed are well known in the art, for example, the lens system including optical zone, haptic rims, tabs and loops can be made from any optically clear plastic material such as polymethylmethacrylate resin (Perspec CQ, Imperial Chemical Industries, Ltd., Great Britain). The pins are preferably made from an inert metal such as platinum or titanium or from a polymeric material such as isotatic polypropylene.

Preferably, the optical zone is formed of an optically clear plastic polymeric material such as polymethylmethacrylate and the haptic parts including haptic rims loop and tabs can be made of polypropylene. Polymethylmethacrylate having a density of approximately 1.12 and polypropylene having a density of approximately 0.91 would provide a lens system having a density approaching that of the aqueous median in which the lens is surrounded in the eye and hence would the lens be essentially weightless within the eye.

In operation, the tab extensions and particularly the positioning of the pins within the tabs should be such that the pin penetrates the iris beyond the sphincter and dilator muscles of the eye.

Figure 18:
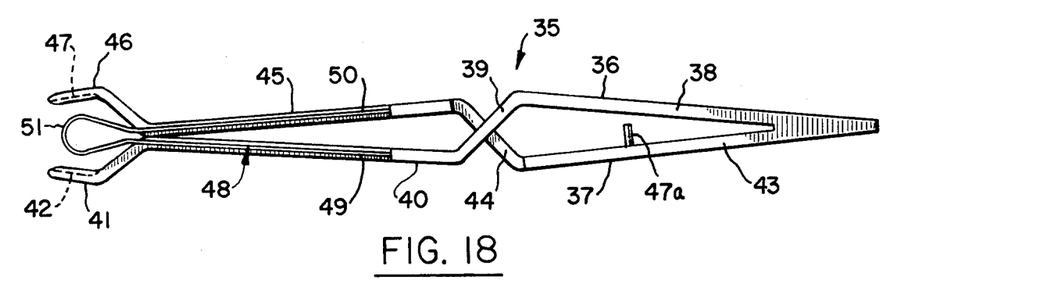
FIG. 18 is a plan view of tweezers employed in this invention.
Figure 19:
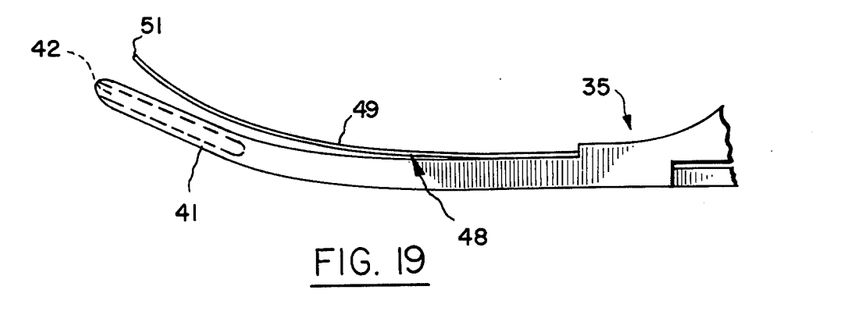
FIG. 19 is an enlarged partial side view of the gripping portion of the tweezers.

Illustrated in FIGS. 18 and 19 is a tool 35 particularly adapted for use in the insertion of, for instance, assembly illustrated in FIG. 2. Tool 35 includes first 36 and second 37 spring members. Member 36 includes a first portion 38, a second portion 39 and a third portion 40.

The free end of third portion 40 includes a gripping portion 41 having a groove 42 (FIG. 20) provided therein. Member 37 includes a first portion 43, a second portion 44 and a third portion 45. As with member 36, the free end of portion 45 is provided with gripping portion 46 having a groove 47 provided therein. Member 37 also includes a stub pin 47a to limit the relative inward movement between members 36 and 37. As is evident from inspection of FIGS. 18 and 19 groove 42 and 47 are dramatically opposed for gripping a tab member, such as tab 3 (FIG. 1) therebetween. As is also evident from inspection of FIGS. 18 and 19, attached to third portions 40 and 45 is a generally elongated, U-shaped actuator member 48, including leg portions 49 and 50 and cross member 51. Member 48 is made of spring material with, as illustrated in FIG. 19 cross member 51 biased away from gripping portions 41 and 46.

As those skilled in the art will appreciate, member 48 may be replaced with, for instance, a single elongated member attached to one of third portions 40, 45 and having an L or T-shaped free end.

Figure 20:
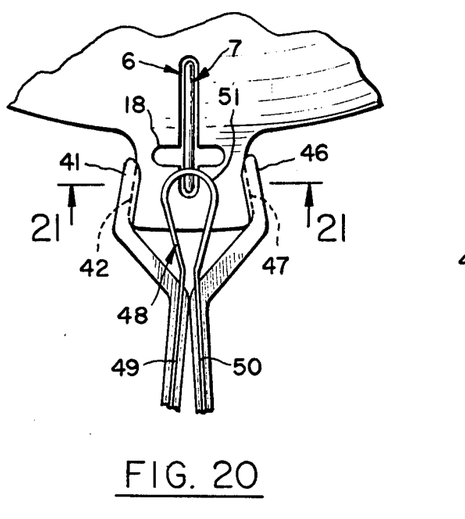
FIG. 20 shows the tweezers gripping the lens tab.
Figure 21:
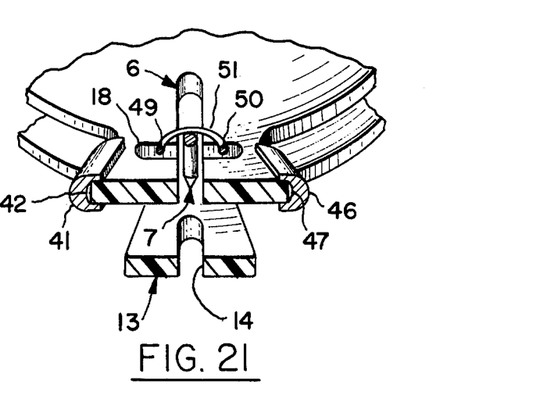
FIG. 21 is a section along line 21—21 of FIG. 20.

In operation, tab 3 illustrated in, for example, FIG. 1 is held in grooves 42 and 47 of gripping portions 41 and 46, as illustrated in FIGS. 20 and 21. The spring tension of members 36 and 37 in conjunction with the configuration of gripping portions 41, 46 and the configuration of tab 3 insure that tab 3 is securely held without any pressure applied to holding portions 38 and 43. With the cornea held back and the natural lens removed, the lens system is inserted in the eye so that tab pairs 3 and 13 capture the iris therebetween. Any further support means are also properly positioned. With the lens system positioned, pressure is then applied to actuator member 48 which forces pin 7 through the iris and into opening 4 provided in tab 13 to securely hold the lens system within the eye.

It will be apparent to those skilled in the art that various modifications of the artificial intraocular lens described herein can be made without departing from the spirit and scope of the invention. For instance, the number of anterior and posterior tabs for positioning a pin perpendicular therein may be varied. Materials other than those described herein may be suitably employed for forming the artificial intraocular lens systems, the materials disclosed herein merely being illustrative. The dimensions of the artificial intraocular lenses may be changed as required by the operating physician and the patient to be fitted.

I claim:

1. In an artificial intraocular lens system for insertion into the eye including an optical zone and means for supporting the lens in the eye, the improvement comprising at least one pair of anterior and posterior tabs extending from the periphery of the optical zone said tabs being spaced apart a sufficient distance to smoothly receive and channel a portion of the iris therebetween without interfering with the dilation and constriction of said iris, the anterior tab including groove means for receiving and allowing the passage of a pin therethrough, said tabs being adapted to hold the pin substantially perpendicular therebetween, thereby transiridially fixing the lens in the eye.

2. The invention according to claim 1 further including a pin having a point at one end to puncture the iris, said pin being of a sufficient length to extend between the posterior and anterior tabs after such puncture.

3. In an artificial intraocular lens system for insertion in the eye including an optical zone and means for supporting the lens in the eye, the improvement comprising the combination of:
(a) at least one pair of tabs comprising an anterior and a posterior tab extending from the circumferential edge of the optical zone and spaced apart a distance sufficient to receive a portion of the iris therebetween, the anterior tab including an opening near its edge for the passage of a pin therethrough, said posterior tab adapted to receive the free end of a pin, said tabs further adapted to hold a pin substantially perpendicular therebetween so as to be capable of transiridially fixing the lens in the eye; and
(b) a pin having a substantially straight first portion and a hooked portion for insertion between the tabs, said straight portion of the pin having one end extended into the pivotably secured into the anterior side of the lens system at a substantial distance inwardly of the tab edge, said straight portion of the pin extending acutely from the tab surface and hook shaped at the free end, said pin being of a sufficient length whereby upon inwardly pivoting the pin the hooked portion passes through said opening of the anterior tab and is received by the posterior tab.

4. The intraocular lens of claim 3 wherein the secured end of the pin is enlarged and rounded and anchored in a depression in the shape of a socket of the anterior tab thereby providing a ball and socket joint.

5. The intraocular lens of claim 3 wherein the anterior tab is provided with a depressed hinge pin at a substantial distance inwardly of the tab edge and the fixed end of the pin is pivotably secured thereto.

6. The intraocular lens of claim 3 wherein the pin is malleable and the fixed end is bendably pivotable.

7. The intraocular lens of claim 3 wherein the pin is formed of a metal and the tabs and optical zone are formed of a plastic material.

8. The intraocular lens of claim 3 wherein the pin is formed of a metal, the optical zone is formed of polymethylmethacrylate and the tabs are formed of polypropylene.

9. The intraocular lens of claim 3 wherein the anterior tab is provided with a groove running longitudinally and of sufficient length whereby upon fully pivoting the pin said straight portion is substantially flush with the surface of the tab.

10. The intraocular lens of claim 9 wherein the anterior tab further includes a slot running transverse the groove said slot being inwardly from the opening for the pin.

11. The intraocular lens of claim 3 wherein the means for supporting the lens in the eye includes a pair of posterior loops having their ends affixed to the optical zone at significant distance inwardly from the peripheral edge of said lens, said loops extending in generally opposite directions, said supporting means further including an anterior rod or tab extending generally in the opposite direction from the tab and pin combination.

12. The intraocular lens of claim 3 wherein the supporting means further includes anterior and posterior haptic rims connected to and continuous with at least a major portion of the circumference of the optical zone.

13. The intraocular lens of claim 12 wherein the haptic rims further include tabs extending generally in the opposite direction from the tab and pin combination.

14. The intraocular lens of claim 13 wherein the haptic rim is annular in shape and has a U-shaped cross-section the inner portion being provided with an annular groove for receiving and locking into place an optical lens.

15. An artificial intraocular lens system for insertion in the eye including an optical portion and a lens support portion, said lens support portion including anterior and posterior haptic rims connected to and contiguous with at least a major portion of the circumference of said optical portion and spaced apart a distance sufficient to receive a portion of the iris therethrough, said anterior and posterior haptic rims each including at least one tab portion extending from the edge of the rim, said support portion further including a pin having a substantially straight portion and a hook portion one end of said straight portion extended into and bendably secured into the anterior side of the anterior haptic rim at a substantial distance inwardly from the tab edge, the other end connected to the hook portion by a bight portion, said hook portion being at an angle of generally 90° to the straight portion, said anterior tab including an opening near the edge for the passage of the hook portion of the pin, said operator tab adapted to receive the free end of the pin, said pin extending acutely from the tab surface, said pin being of sufficient length whereby upon inwardly bending the pin the hook portion passes through the hole of the anterior tab and is received by the posterior tab.

16. The lens of claim 15 wherein the posterior and anterior tab portions are adapted to hold the hook portion generally perpendicular therebetween.

17. The lens of claim 15 wherein the anterior tab portion together with the haptic rim portion contiguous thereto contains a groove running longitudinally and of sufficient length whereby upon fully inwardly bending the pin, said straight portion is generally flush with the surface of the lens system, said tab portion further including a slot transverse the longitudinal groove.

18. The lens of claim 15 wherein the optical portion comprises a high plus lens spaced apart from a plano lens, the space therebetween being airtight.

19. The lens of claim 15 wherein the optical portion is formed of an optically clear plastic material and the rim and tab portions are formed of polypropylene and the pin is formed of a metal.

20. The lens of claim 19 wherein the plastic material is polymethylmethacrylate.

21. An artificial intraocular lens system for insertion in the eye including an optical portion and a lens support portion, said lens support portion including an anterior haptic rim connected to and continuous with at least a major portion of the circumference of said optical portion, said haptic rim including at least one anterior tab portion extended from the edge of the rim, said support portion further including a pin having a substantially straight portion and a hook portion, one end of said straight portion extended into and bendably secured into the anterior side of the haptic rim at a substantial distance inwardly from the anterior tab edge, the other end connected to the hook portion by a bight portion, said hook portion being at an angle of generally 90° to the straight portion, said anterior tab portion including an opening near the edge for the passage of the hook portion of the pin, said lens support portion further including posterior loop means having at least two legs extending therefrom and affixed to the optical zone at a significant distance inwardly from the peripheral edge of said lens, said loop means extending generally at about 90° with relation to said anterior tab portion, said loop means further extending into a tab portion oppositely disposed from and spaced apart from said anterior tab portion, said posterior tab portion adapted to receive the free end of the pin, said pin extending acutely from the anterior tab surface, said pin being of sufficient length whereby upon inwardly bending the pin, the hook portion passes through the hole of the anterior tab and is received by the posterior tab.

22. The lens of claim 21 further including an anterior tab oppositely disposed from the anterior tab and pin combination.

23. The lens of claim 21 wherein the spaced apart tab portions are adapted to hold the hook portion generally perpendicular therebetween.

24. The lens of claim 21 wherein the anterior tab portion together with the haptic rim portion contiguous thereto contains a groove running longitudinally and of sufficient length whereby upon fully inwardly bending the pin, said straight portion is generally flush with the surface of the lens system, said tap portion further including a slot transverse the longitudinal groove.

25. The lens of claim 21 wherein the optical portion is formed of an optically clear plastic material the pin of a metal and the remainder of the lens support portions are formed of polypropylene.

26. The lens of claim 25 wherein the plastic material is polymethylmethacrylate.

27. A method of inserting an intraocular lens system having an engagable tab into an eye with a tool including first, second and third relatively movable members, said first and second members adapted to hold said tab provided on said intraocular lens system therebetween, said third member adapted, when said first and second members grip said tab, for engagement with a pin provided on said intraocular lens assembly to move said pin relative to said tab, said method comprising the steps of:
  (a) gripping said tab;
  (b) inserting said lens assembly into said eye with said tab member capturing said iris; and
  (c) moving said third member relative to said first and second members to push said pin means through said iris.

* * * * *

UNITED STATES PATENT AND TRADEMARK OFFICE
CERTIFICATE OF CORRECTION

PATENT NO. : 4,124,905
DATED : November 14, 1978
INVENTOR(S) : James A. Clark

It is certified that error appears in the above-identified patent and that said Letters Patent are hereby corrected as shown below:

Sheet 2, Figure 7, please delete numeral "19"

Signed and Sealed this

Twentieth Day of February 1979

[SEAL]

Attest:

RUTH C. MASON
Attesting Officer

DONALD W. BANNER
Commissioner of Patents and Trademarks